United States Patent [19]

Pilgram et al.

[11] 4,345,076

[45] Aug. 17, 1982

[54] CERTAIN HERBICIDAL N-(PARA-(6-CHLORO-3-PYRIDAZINYLOXY)PHENYL)TRIFLUOROMETHANESULFONAMIDES

[75] Inventors: Kurt H. Pilgram; Richard D. Skiles, both of Modesto, Calif.

[73] Assignee: Shell Oil Company, Houston, Tex.

[21] Appl. No.: 118,353

[22] Filed: Feb. 4, 1980

[51] Int. Cl.$^3$ ............................................. C07D 237/14
[52] U.S. Cl. ......................................... 544/241; 71/92
[58] Field of Search ........................................ 544/241

[56] References Cited

U.S. PATENT DOCUMENTS

| | | | |
|---|---|---|---|
| 3,652,257 | 3/1972 | Jojina | 544/241 |
| 3,686,192 | 8/1972 | Moore | 546/293 |
| 3,840,597 | 10/1974 | Moore | 544/107 |
| 3,906,024 | 9/1975 | Moore | 260/465 E |

OTHER PUBLICATIONS

Moore et al., IV Chem. Abs. 78, 43073d, (1972).

Primary Examiner—Mark L. Berch

[57] ABSTRACT

Certain N-(para-(6-chloro-3-pyridazinyloxy)phenyl)trifluoromethanesulfonamides and their use as herbicides.

1 Claim, No Drawings

CERTAIN HERBICIDAL N-(PARA-(6-CHLORO-3-PYRIDAZINYLOXY)-PHENYL)TRIFLUOROMETHANESULFONA-MIDES

DESCRIPTION OF THE INVENTION

It has been found that useful herbicidal properties are possessed by certain sulfonamides of the formula:

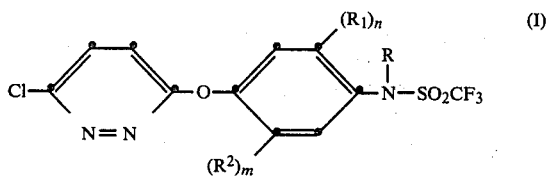

wherein R is hydrogen or $-SO_2CF_3$, m and n each is zero or one, and $R^1$ and $R^2$ each is chlorine, fluorine or methyl.

Typical, exemplary individual species of the class of compounds, the manner in which they can be prepared and isolated, and summaries of the results of their herbicidal testing, are set forth in the Examples hereinafter. Other, typical individual species of the class are the following (in which the symbols refer to Formula I):

| R | n | $R^1$ | m | $R^2$ |
|---|---|---|---|---|
| H | 1 | Cl | 1 | Cl |
| H | 1 | $-CH_3$ | 1 | Cl |
| H | 1 | F | 1 | F |
| H | 1 | Cl | 1 | $-CH_3$ |

The compounds of Formula I can be prepared by the following general sequence of reactions:

(a) treating a mixture of 3,6-dichloropyridazine and the appropriate para-aminophenol

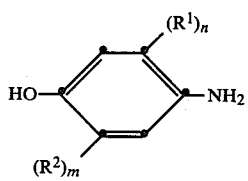

in a solvent such as dimethyl sulfoxide with a strong base, such as sodium hydride, to form the corresponding 4-(6-chloro-3-pyridazinyloxy)benzeneamine;

(b) treating a chilled solution of the amine in a solvent, such as methylene chloride, with trifluoromethanesulfonic anhydride in the presence of, or then adding, a nitrogen base, such as triethylamine.

Some of the aminophenol precursors are known compounds; the others can be prepared by known methods.

The preparation of typical, exemplary individual species of the compounds of Formula I is shown in the following examples. In each case, the identity of the product, and of each intermediate involved, was confirmed by appropriate elemental and spectral analyses.

EXAMPLE 1

N-(3-chloro-4-(6-chloro-3-pyridazinyloxy)phenyl)-1,1,1-trifluoromethanesulfonamide (1) and N,N-bis(3-chloro-4-(6-chloro-3-pyridzainyloxy)-phenyl)-1,1,1-trifluoromethanesulfonamide (2)

A solution of 86.8 g of 2-chloro-4-nitrophenol in 200 ml of tetrahydrofuran containing 2 g of Raney nickel catalyst was hydrogenated in a Parr shaker at 50 p.s.i. hydrogen pressure. The mixture was filtered and the solvent was evaporated from the filtrate. The residue was recrystallized from ether to give 4-amino-2-chlorophenol (1A), as a tan solid, mp: 144°-147° C.

12 g of sodium hydride was added in portions to a stirred solution of 71.8 g of 1A and 25 g of 3,6-dichloropyridazine in 300 ml of dimethyl sulfoxide, the temperature of the mixture being held at 50° C. The mixture then was stirred for one hour and poured into ice water. The mixture was slightly acidified with dilute hydrochloric acid, and was extracted with methylene chloride. The extract was washed with water, dried (magnesium sulfate) and the solvent was evaporated to give 4-(6-chloro-3-pyridazinyloxy)benzeneamine (1B), as a tan solid, mp: 126°-129° C.

7 g of trifluoromethanesulfonic anhydride was added over a 5-minute period to a chilled (−10° C.), stirred solution of 6.4 g of 1B in 100 ml of methylene chloride. The resulting mixture was stirred at room temperature for 30 minutes, then cooled to −10° C. and held there while 2.5 g of triethylamine was added. The resulting mixture was warmed to and held at room temperature for 30 minutes, and mixed with 100 ml of cold dilute hydrochloric acid. The organic phase was separated, dried (magnesium sulfate), and solvent was evaporated. The residue was chromatographed over silica gel, using a 4:30:66 (v/v/v) mixture of tetrahydrofuran, ethyl acetate and hexane as eluent, to give two fractions: 1, as an amber syrup, and 2 as a cream-colored solid, mp: 120°-122° C.

EXAMPLES 2 AND 3

By the methods described in Example 1, there were prepared the individual species wherein (referring to Formula I):

Example 2 (Compound 3): $R=-SO_2CF_3$, m and n=0, as a colorless solid, mp: 125°-127° C.;

Example 3 (Compound 4): R=H, m and n=0, as an off-white solid, mp: 172°-174° C.

EXAMPLE 4

N-(4-(6-chloro-3-pyridiazinyloxy)-2,5-dimethylphenyl)-1,1,1-trifluoromethanesulfonamide (5)

4.8 g of sodium hydride was added in portions to a stirred solution of 30 g of 3,6-dichloropyridazine and 27.4 g of 4-amino-2,5-dimethylphenol in 300 ml of dimethyl sulfoxide. The temperature of the mixture rose to 65° C. The mixture was then stirred for 18 hours at room temperature, poured over ice water and filtered. Recrystallization of the filter cake from methanol gave 4-(6-chloro-3-pyridazinyloxy)-2,5-dimethylbenzeneamine, as a brown solid (5A), mp: 138°-140° C.

20.9 g of trifluoromethanesulfonic anhydride was added drop-by-drop over a 10-minute period to a chilled (−20° C.) stirred solution of 18.6 g of 5A and 7.5 g of triethylamine in 200 ml of methylene chloride. The mixture then was warmed to and stirred at ambient temperature for 2 hours, and diluted with water. The organic phase was separated, dried (magnesium sulfate), and the solvent was evaporated. The residue was recrystallized from 1:1 (v/v) ether/hexane to give 5, as a tan solid, mp: 155°–157° C.

EXAMPLES 5 AND 6

By the method described in Example 4, there were prepared the individual species wherein (referring to Formula I):

Example 5 (Compound 6): R=H, m=0, n=1, $R^1$=—$CH_3$, as an off-white solid, mp: 134°–136° C.;

Example 6 (Compound 7): R=H, m=0, n=1, $R^1$=Cl, is an off-white solid, mp: 143°–146° C.

Compounds of Formula I have been found to be useful for killing unwanted plants, being active with respect to both broad-leaved plants and grasses, and being effective when applied either preemergence (applied to the soil before the plants have sprouted) or postemergence (to the foliage of the growing plants).

Accordingly, the invention includes a method of killing unwanted plants which comprises applying to the locus an effective amount of a compound of Formula I. Likewise the invention also includes herbicidal compositions comprising a carrier or a surface-active agent, or both a carrier and a surface-active agent, and, as active ingredient at least one compound of Formula I.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as for example, isopropanol, glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosene, light mineral oils; chlorinated hydrocarbons, such as for example, carbon tetrachloride, perchloroethylene, trichloroethane, including liquefied normally vaporous gaseous compounds. Mixtures of different liquids are often suitable. The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, nonsedimenting, flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick mayonnaise-like consistency.

The compositions of the invention may also contain other ingredients, for example, other compounds possessing pesticidal, especially insecticidal, acaricidal, herbicidal or fungicidal properties.

Protection of a locus or area from undesirable plants is effected by applying a compound of Formula I, ordinarily in a composition of one of the aforementioned types, to the foliage of the plants or plant growth medium, e.g., soil in which the plant is growing or in which the seeds are present. The active compound, of course, is applied in an amount sufficient to exert the desired action.

The amount of compound of the invention to be used in controlling undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kilograms per hectare of the compound of Formula I will be satisfactory.

Examples of Herbicidal Activity

The preemergence herbicidal activity of the compounds of the invention was evaluated by planting seeds of water grass (*Echinochloa crus-galli*), garden cress (*Lepidium sativum*), downy brome (*Bromus tectorum*), velvetleaf (*Abutilon theophrasti*), yellow foxtail (*Setaria lutescens*), and sicklepod (*Cassia obtusifolia*) in test tubes, nominally measuring 25×200 millimeters, filled about three-quarters full of untreated soil, in each case covered on top with about 2.5 cubic centimeters of soil treated with the test compound at the rate of 0.1 and 1 milligram per tube, designated in Table I at Rates I and II, respectively. The dosages of test compound were approximately two and twenty pounds of test compound per acre, respectively. The seeds were planted in the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Living tissue, but plant expected to die |
| 7 | Plant badly damaged, but expected to live |
| 6 | Plant badly damaged, but expected to recover completely |
| 5 | Unacceptable damage for crop plants, insufficient damage to weeds |
| 3–4 | Definite damage |
| 1–2 | Plant slightly affected, possibly by the chemical, possibly due to biological variability |
| 0 | No visible effect |

The postemergence activity of the compounds of this invention was evaluated by spraying 10-day old large crabgrass (*Digitaria sanguinalis*) plants, 13-day old redroot pigweed (*Amaranthus retroflexus*) plants, 6-day old Johnsongrass (*Sorghum halopense*) plants, 9-day old velvetleaf plants, 9-day old yellow foxtail plants and 9-day old sicklepod plants to runoff with a liquid formulation of the test compound at the rates of 2.4 milliliters of a 0.025% solution (about one pound of Compound I per acre), designated Rate I in Table I, and 2.4 milliliters of a 0.25% solution (about ten pounds of Compound I per acre), designated Rate II in Table I. The sprayed plants were held under controlled conditions of temperature, moisture and light for 7 to 8 days and the effect of Compound I was then evaluated visually, the results being rated on the 0 to 9 scale described above.

The results of the tests are summarized in Table I.

TABLE I

HERBICIDE SCREEN RESULTS

| | Preemergence (Soil) | | | | | | | | | | | | Postemergence (Foliar) | | | | | | | | | | | |
|---|---|---|---|---|---|---|---|---|---|---|---|---|---|---|---|---|---|---|---|---|---|---|---|---|
| | Water Grass | | Garden Cress | | downy Brome | | Velvet-leaf | | Yellow Foxtail | | Sickle-pod | | Crab-grass | | Pig-weed | | Johnson-grass | | Velvet-leaf | | Yellow Foxtail | | Sickle-pod | |
| | | | | | | | | | | | | | Dosage | | | | | | | | | | | |
| Compound | I | II | I | II | I | II | I | II | I | II | I | II | I | II | I | II | I | II | I | II | I | II | I | II |
| 1 | 7 | 8 | 7 | 9 | 9 | 9 | 7 | 9 | 7 | 8 | 0 | 7 | 7 | 8 | 5 | 7 | — | | 7 | 8 | 8 | 9 | 6 | 9 |
| 2 | 8 | 8 | 8 | 9 | 9 | 9 | 7 | 7 | 7 | 8 | 5 | 6 | 7 | 7 | 7 | 8 | 7 | 7 | 6 | 6 | 7 | 7 | 7 | 7 |
| 3 | 7 | 8 | 7 | 9 | 7 | 9 | 6 | 7 | 7 | 7 | 2 | 2 | 7 | 7 | 6 | 7 | 7 | 7 | 0 | 3 | 7 | 7 | 3 | 4 |
| 4 | 8 | 9 | 8 | 9 | 9 | 9 | 7 | 7 | 7 | 8 | 2 | 6 | 7 | 8 | 3 | 9 | 7 | 8 | 0 | 6 | 7 | 8 | 3 | 9 |
| 5 | 7 | 8 | 5 | 9 | 9 | 9 | 5 | 7 | 4 | 7 | 4 | 6 | 7 | 8 | 6 | 9 | 8 | 8 | 2 | 7 | 2 | 7 | 7 | 8 |
| 6 | 7 | 8 | 7 | 9 | 8 | 9 | 5 | 9 | 4 | 8 | 2 | 6 | 7 | 8 | 7 | 9 | 7 | 9 | 7 | 7 | 7 | 8 | 6 | 9 |
| 7 | 8 | 9 | 8 | 9 | 8 | 9 | 6 | 8 | 7 | 8 | 3 | 7 | 7 | 8 | 2 | 7 | 8 | 8 | 5 | 8 | 7 | 8 | 7 | 8 |

We claim:

1. A compound of the formula:

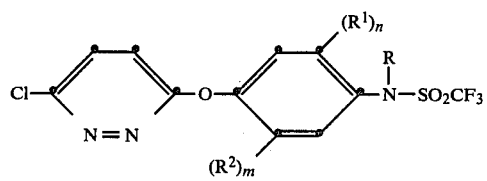

wherein R is hydrogen or —SO$_2$CF$_3$, m and n each is zero or one, and R$^1$ and R$^2$ each is chlorine, fluorine or methyl.

* * * * *